(12) United States Patent
Deng

(10) Patent No.: US 11,866,135 B1
(45) Date of Patent: Jan. 9, 2024

(54) AUXILIARY EQUIPMENT FOR SWIMMING

(71) Applicant: Shenzhen Junmanda Technology Co., Ltd., Guangdong (CN)

(72) Inventor: Shidong Deng, Guangdong (CN)

(73) Assignee: Shenzhen Junmanda Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/344,970

(22) Filed: Jun. 30, 2023

(51) Int. Cl.
| | |
|---|---|
| *B63C 9/125* | (2006.01) |
| *B63C 9/18* | (2006.01) |
| *B63C 9/20* | (2006.01) |
| *A61B 5/02* | (2006.01) |
| *A61B 5/024* | (2006.01) |

(52) U.S. Cl.
CPC ........ *B63C 9/1255* (2013.01); *A61B 5/02438* (2013.01); *B63C 9/18* (2013.01); *B63C 9/20* (2013.01)

(58) Field of Classification Search
CPC ........... B63C 9/00; B63C 9/08; B63C 9/1255; B63C 9/16; B63C 9/18; B63C 9/20; A61B 5/02438
USPC ......................................................... 441/89
See application file for complete search history.

(56) References Cited

U.S. PATENT DOCUMENTS

| | | | | |
|---|---|---|---|---|
| 1,488,049 A * | 3/1924 | Lawless | ................. | B63C 9/155 441/122 |
| 4,813,899 A * | 3/1989 | Fujimoto | ................ | B63C 9/155 441/122 |
| 5,368,512 A * | 11/1994 | Brown | .................... | B63C 9/155 441/108 |
| 5,702,279 A * | 12/1997 | Brown | .................... | B63C 9/155 441/108 |
| 6,620,010 B2 * | 9/2003 | Noonan | ................ | B63C 9/1255 441/106 |

* cited by examiner

*Primary Examiner* — Lars A Olson

(57) ABSTRACT

The present disclosure provides a swimming auxiliary equipment, including an auxiliary equipment main body, a strap, a connecting belt and two arm jackets, wherein two sides of the auxiliary equipment main body are tied to the waist of a swimmer through the strap, and the arm jackets are connected to the auxiliary equipment main body through the connecting belt; the auxiliary equipment main body includes a first air bag, a cavity is arranged inside a waterproof layer, the first air bag is arranged in the cavity, and a pressure sensor is arranged on an inner wall of the auxiliary equipment main body; and the auxiliary equipment main body includes an expansion bin arranged in the cavity and a net structure with a plurality of connected layers, a priming device is arranged on the net structure, and the priming device is arranged in the cavity and connected to the pressure sensor.

10 Claims, 4 Drawing Sheets

AUXILIARY EQUIPMENT FOR SWIMMING

TECHNICAL FIELD

The present disclosure relate to swimming devices, especially to a swimming auxiliary equipment.

BACKGROUND

When a beginner, specifically a child learns to swim, the auxiliary equipment is an essential tool, through which the beginner may be familiar with the buoyancy and resistance of water and not fear the water. Even users have learned to swim, the safety of swimmers can be further ensured by using the swimming auxiliary equipment. The swimming auxiliary equipment is usually taken along, widely applied in the water transport industry, water work, water sports, water entertainment and other activities, and can provide stable buoyancy to the swimmers, so as to increase its use and safety performances. During use, the auxiliary equipment main body is tied to the waist of the swimmer by a strap, and two arm jackets are respectively installed on two upper arms of the swimmer. Normally, the buoyancy provided by the swimming auxiliary equipment is equal to the gravity of the human body, so that the swimmer is always floating in the water. However, when air leakage occurs to the swimming auxiliary equipment, the buoyancy provided by the swimming auxiliary equipment will drop sharply; and when the buoyancy provided by the swimming auxiliary equipment is not enough to balance the gravity of the human body, the swimmer will sink in the water, resulting in safety accidents.

SUMMARY

Embodiments of the present disclosure provide a swimming auxiliary equipment, to solve the problem of being prone to safety accidents when air leakage occurs to the existing auxiliary equipment.

Embodiments of the present disclosure provide a swimming auxiliary equipment, including an auxiliary equipment main body, a strap, a connecting belt and two arm jackets. Two sides of the auxiliary equipment main body are tied to the waist of a swimmer through the strap, and the two arm jackets are all connected to the auxiliary equipment main body through the connecting belt; the auxiliary equipment main body includes a waterproof layer and a first air bag, a cavity is arranged inside the waterproof layer, the first air bag is arranged in the cavity and connected to an outside air pump through an inflatable head, a pneumatic one-way valve is arranged on the inflatable head, and a pressure sensor is arranged on an inner wall of the auxiliary equipment main body; and the auxiliary equipment main body further includes an expansion bin, which is arranged in the cavity and includes a net structure with a plurality of connected layers, the net structure is a flexible structure, a priming device is connected to the net structure and arranged in the cavity, and the priming device is in signal connection with the pressure sensor.

Further, the priming device includes a sealing cover, a liquid storage tube and a mixing tube, a top end of the liquid storage tube is connected to the sealing cover, a bottom end of the liquid storage tube is connected to a top end of the mixing tube, a bottom end of the mixing tube is connected to the net structure, and a pick is also connected between the liquid storage tube and the mixing tube; and a first foaming liquid tube and a second foaming liquid tube that are independent of each other are arranged in the liquid storage tube, a top end of the first foaming liquid tube and a top end of the second foaming liquid tube are all in sealing connection with the sealing cover, a bottom end of the first foaming liquid tube and a bottom end of the second foaming liquid tube all resist to the pick, a first through hole and a second through hole that adapt to the bottom end of the first foaming liquid tube and the bottom end of the second foaming liquid tube are formed in the pick, an upper surface of the pick is connected to a rotary motor, a first controller is arranged in the rotary motor, and the first controller is in communication connection with the pressure sensor.

Further, an electric motor is arranged at the lower part of the pick, and the electric motor is connected to an agitating vane through a rotary shaft; and when the first through hole and the second through hole on the pick rotate until to be aligned with the bottom end of the first foaming liquid tube and the bottom end of the second foaming liquid tube, liquid in the first foaming liquid tube and the second foaming liquid tube flows into the mixing tube, and the electric motor drives the agitating vane to rotate.

Further, the strap includes a first waistband and a second waistband, one end of the first waistband is connected to the auxiliary equipment main body, and the other end of the first waistband is provided with a slot; and one end of the second waistband is connected to the auxiliary equipment main body, the other end of the second waistband is provided with a buckle, and the buckle is clamped in the slot.

Further, outer walls of the first waistband and the second waistband are all connected to a second air bag, an outer wall of the auxiliary equipment main body is connected to a third air bag, and an outer wall of the second air bag and an outer wall of the third air bag are all provided with gas injection devices.

Further, each gas injection device includes a gas storage tank, a rotary rod and a motor, diaphragms are arranged between the gas storage tank and the second air bag as well as between the gas storage tank and the third air bag, the motor is arranged on an inner wall of the gas storage tank, an input end of the motor is connected to a second controller, the second controller is in communication connection with the pressure sensor, an output end of the motor is connected to the rotary rod, and the rotary rod resists to the diaphragms.

Further, a plurality of first air flotation bins are uniformly arranged on the second air bag, a plurality of second air flotation bins are uniformly arranged on the outer wall of the third air bag, the first air flotation bins are communicated with the second air bag, and the second air flotation bins are communicated with the third air bag; and the first air flotation bins and the second air flotation bins are located on the same plane, and the volume of the second air flotation bins is greater than that of the first air flotation bins.

Further, inner walls of the arm jackets are provided with heart rate sensors, which are in communication connection with the second controller.

Further, the connecting belt is an annular belt, on which a lock catch is arranged.

Further, a safety module is arranged in the auxiliary equipment main body, and the safety module includes a voice prompt module, a vital sign monitoring module and a help module; and an output end of each heart rate sensor is connected to an input end of the vital sign monitoring module, an output end of the vital sign monitoring module is in communication connection with an input end of the help module, and an output end of the help module is in communication connection with the voice prompt module.

According to the swimming auxiliary equipment provided by embodiments of the present disclosure, when air leakage occurs to the swimming auxiliary equipment, the pressure sensor may feed the pressure change of the auxiliary equipment main body back to the priming device, the priming device can inject a foaming agent to the multi-layer net structure in the expansion bin, the net structure expands quickly after the foaming agent reacts, so as to compensate the volume of the auxiliary equipment main body and recover the buoyancy provided by the auxiliary equipment to be normal. During use, the multi-layer net structure is formed with a shape that adapts to the body of the user. After the foaming agent on the multi-layer net structure is solidified, the expanded foaming structure fits with the body of the user well, on the one hand, the structural strength of the auxiliary equipment can be improved to avoid breakage, and on the other hand, the fit between the auxiliary equipment and the user can be improved to avoid shifting and falling, thereby increasing the use and safety performances of the auxiliary equipment.

BRIEF DESCRIPTION OF THE DRAWINGS

To better clarity the technical solution of the embodiments of the present disclosure, the drawings required to illustrate the embodiments will be simply described blow. It is apparent that the drawings described below merely illustrate some embodiments of the embodiments of the disclosure. Those skilled in the art can obtain other drawings without creative labor on the basis of those drawings.

To more completely understand the present disclosure and its beneficial effects, description will be carried out in detail below in conjunction with the drawings. The same reference sign in the description below indicates the same part.

Figure 1:
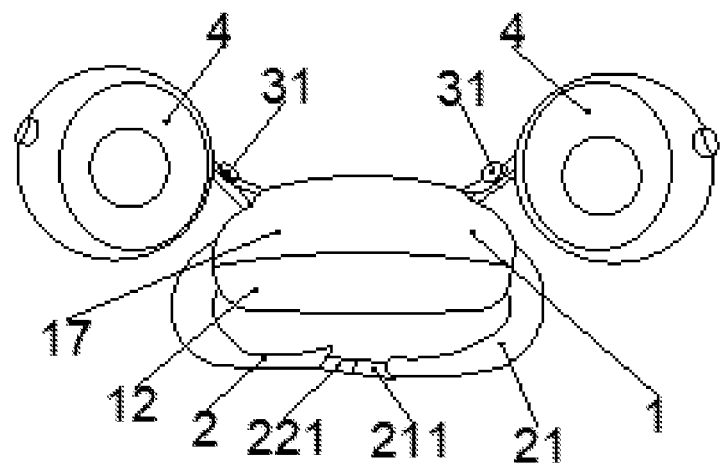
FIG. 1 is a structural schematic diagram of a swimming auxiliary equipment provided by embodiments of the present disclosure.

1. Auxiliary equipment main body, 11. Waterproof layer, 12. First air bag, 13. Cavity, 14. Inflatable head, 15. Pneumatic one-way valve, 16. Pressure sensor, 17. Expansion bin, 171. Net structure, 18. Second air flotation bin, 2. Strap, 21. First waistband, 211. Slot, 22. Second waistband, 221. Buckle, 23. Second air bag, 24. First air flotation bin, 25. Third air bag, 3. Connecting belt, 31. Lock catch, 4. Arm jacket, 41. Heart rate sensor, 5. Priming device, 51. Sealing cover, 52. Liquid storage tube, 521. First foaming liquid tube, 522. Second foaming liquid tube, 53. Mixing tube, 54. Pick, 541. First through hole, 542. Second through hole, 55. Rotary motor, 551. First controller, 56. Agitating vane, 6. Gas injection device, 61. Gas storage tank, 62. Rotary rod, 63. Motor, 64. Second controller, 65. Diaphragm, 7. External trigger button.

DETAILED DESCRIPTION OF THE EMBODIMENTS

In order to make those skilled in the art understand the technical solutions of the present disclosure better, the technical solutions in the embodiments of the present disclosure are clearly and completely elaborated below in combination with the drawings. It is apparent that the described embodiments are only a part of the embodiments of the present disclosure but not all. Based on the embodiments of the present disclosure, all the other embodiments obtained by those of ordinary skill in the art on the premise of not contributing creative effort should belong to the protection scope of the present disclosure.

It is noted that the description that an element is "fixed on" or "set on" another component may refer to that the element is directly or indirectly above another component, and the description that an element is "connected to" another component may refer to that the element is directly or indirectly connected to another component.

It is understood that orientation or position relationships indicated by the terms "length", "width", "upper", "lower", "front", "rear", "left", "right", "vertical", "horizontal", "top", "bottom", "inner", "outer" and the like are based on the orientation or position relationships as shown in the drawings, for ease of describing the present disclosure and simplifying the description only, rather than indicating or implying that the mentioned apparatus or element necessarily has a particular orientation and must be constructed and operated in the particular orientation. Therefore, these terms should not be understood as limitations to the present disclosure.

In addition, the terms "first" and "second" are merely used for description, instead of being understood as indicating or implying relative importance or impliedly indicating the quantity of the showed technical features. Thus, the features defined with "first" and "second" may expressly or impliedly one or more features. In the description of the present disclosure, "multiple" and "a plurality of" mean two or above two, unless specific limitation otherwise.

It is noted that the structure, ratio, size and the like drawn in the drawing of the specification are merely used for cooperating with the content disclosed in the specification, so as to be understood and read by personnel familiar with this technology instead of limiting the implemented limitation conditions to the present disclosure, without substantive technical significance. Modification, proportional relation change or size adjustment of any structure will fall within the scope recorded in the technical content disclosed in the present disclosure without affecting the function and achieved purpose of the present disclosure.

Embodiments of the present disclosure provide a swimming auxiliary equipment, to solve the problem of being prone to safety accidents when air leakage occurs to the existing swimming auxiliary equipment. Description is carried out below in combination with the drawings.

As shown in FIG. 1 to FIG. 5, a swimming auxiliary equipment includes an auxiliary equipment main body 1, a strap 2, a connecting belt 3 and two arm jackets 4. Two sides of the auxiliary equipment main body 1 are tied to the waist of a swimmer through the strap 2, and the two arm jackets 4 are all connected to the auxiliary equipment main body 1 through the connecting belt 3; the auxiliary equipment main body 1 includes a waterproof layer 11 and a first air bag 12, a cavity 13 is arranged inside the waterproof layer 11, the first air bag 12 is arranged in the cavity 13 and connected to an outside air pump through an inflatable head 14, a pneumatic one-way valve 15 is arranged on the inflatable head 14, and a pressure sensor 16 is arranged on an inner wall of the auxiliary equipment main body 1; and the auxiliary equipment main body 1 further includes an expansion bin 17, which is arranged in the cavity 13, a net structure 171 with a plurality of connected layers is arranged in the expansion bin 17, the net structure 171 is a flexible structure, a priming device 5 is connected to the net structure 171 and arranged in the cavity 13, and the priming device 5 is in signal connection with the pressure sensor 16. In some embodiments, the net structure 171 is multi-layer, initial volume of the expansion bin 17 can contain the net structure 171, and the suitable expansion bin 17 is set according to needs. Optionally, the expansion bin 17 and the first air bag 12 are arranged in the front and rear, or the expansion bin 17 is arranged above the first air bag 12.

During use, carbon dioxide is filled in the first air bag 12 through the air pump and the inflatable head 14, the first air bag 12 expands in the cavity 13 of the auxiliary equipment main body 1, so that the volume of the auxiliary equipment main body 1 increases quickly; and the auxiliary equipment main body 1 is tied to the waist or chest of the user through the strap 2, and the two arm jackets 4 are respectively sleeved on the upper arms of two arms of the user. The user enters into the water, normally, the buoyancy provided by the auxiliary equipment is equal to the gravity of the human body, so that the user can swim safely in the water. When air leakage occurs to the auxiliary equipment, the volume of the auxiliary equipment main body 1 will be reduced, and the buoyancy provided by the auxiliary equipment drops sharply; at this time, the pressure sensor 16 can feed the pressure change in the auxiliary equipment main body 1 back to the priming device 5, the priming device 5 can inject a foaming agent to the net structure 171 in the expansion bin 17, the foaming agent expands quickly, correspondingly the expansion bin 17 expands and fills the cavity 13 of the auxiliary equipment main body 1, so as to compensate the volume of the auxiliary equipment main body 1 and recover the buoyancy provided by the auxiliary equipment to be normal; since the net structure 171 is a flexible structure, namely, the net structure 171 has a certain flexibility and the multi-layer net structure 171 is set, the multi-layer net structure 171 is tied to the front of the waist or chest of the user through the auxiliary equipment main body 1 so as to fit with the body of the user well, the multi-layer structure 171 is also formed with a shape fitting with the body of the user, the liquid flowing out of the priming device 5 will be distributed along the net structure 171, when being solidified, the flowing liquid foaming agent will be distributed along the multi-layer net structure 171, so the expanded foaming structure can fit with the body of the user well, on the one hand, the structural strength of the auxiliary equipment can be improved, to avoid breakage, and on the other hand, the fit between the auxiliary equipment and the user can be improved, to avoid shifting and falling, thereby increasing the use and safety performances of the auxiliary equipment.

In this embodiment, when the first air bag 12 is filled with carbon dioxide, the pneumatic one-way valve 15 on the inflatable head 14 can prevent the carbon dioxide from flowing back, so as to ensure the stability of the carbon dioxide in the first air bag 1. In addition, the outermost layer of the auxiliary equipment main body 1 is a waterproof layer 11, which can avoid the water from entering into the auxiliary equipment main body 1.

As shown in FIG. 1 to FIG. 5, in one embodiment, the priming device 5 includes a sealing cover 51, a liquid storage tube 52 and a mixing tube 53, a top end of the liquid storage tube 52 is connected to the sealing cover 51, a bottom end of the liquid storage tube 52 is connected to a top end of the mixing tube 53, a bottom end of the mixing tube 53 is connected to the net structure 171, and a pick 54 is also connected between the liquid storage tube 52 and the mixing tube 53; and a first foaming liquid tube 521 and a second foaming liquid tube 522 that are independent of each other are arranged in the liquid storage tube 52, a top end of the first foaming liquid tube 521 and a top end of the second foaming liquid tube 522 are all in sealing connection with the sealing cover 51, a bottom end of the first foaming liquid tube 521 and a bottom end of the second foaming liquid tube 522 all resist to the pick 54, a first through hole 541 and a second through hole 542 that adapt to the bottom end of the first foaming liquid tube 521 and the bottom end of the second foaming liquid tube 522 are formed in the pick 54, an upper surface of the pick 54 is connected to a rotary motor 55, a first controller 551 is arranged in the rotary motor 55, and the first controller 551 is in communication connection with the pressure sensor 16; and an electric motor is arranged at the lower part of the pick 54, and the electric motor is connected to an agitating vane 56 through a rotary shaft.

In this embodiment, the first foaming liquid tube 521 and the second foaming liquid tube 522 store polyether and isocyanate in respective, and the two kinds of liquid may generate a lot of solid non-toxic foam after being mixed. During use, the bottom end of the liquid storage tube 52 is firstly connected to the top end of the mixing tube 53, so that the pick 54 is fixed between the liquid storage tube 52 and the mixing tube 53; and then the foaming liquid tube 521 with the polyether and the second foaming liquid tube 522 with the isocyanate are put into the liquid storage tube 52, so that the bottom end of the first foaming liquid tube 521 and the bottom end of the second foaming liquid tube 52 resist to the upper surface of the pick 54; afterwards, the top end of the liquid storage tube 52 is sealed through the sealing cover 51; normally, the bottom end of the first foaming liquid tube 521 and the bottom end of the second foaming liquid tube 522 are staggered with the first through hole 541 and the second through hole 542 on the pick 54, so that the bottom end of the first foaming liquid tube 521 and the bottom end of the second foaming liquid tube 522 are in the sealing state; and when air leakage occurs to the auxiliary equipment main body 1, the pressure sensor 16 can transmit the pressure change signal in the auxiliary equipment main body 1 to the first controller 551 in the rotary motor 55 in a wireless form, the first controller 551 can control the rotary motor 55 on the pick 54 to rotate, the rotary motor 55 can drive the pick 54 to rotate according to a setting angle, so that the first through hole 541 and the second through hole 542 on the pick 54 rotate until to be aligned with the bottom end of the first foaming liquid tube 521 and the bottom end of the second foaming liquid tube 522, the first foaming liquid tube 521 and the second foaming liquid tube 522 are conducted with the mixing tube 53, and the polyether in the first foaming liquid tube 521 and the isocyanate in the second foaming liquid tube 522 flow into the mixing tube 53 and react, so as to obtain polyurethane foam. The electric motor is installed on the inner wall of the mixing tube 53, when the first through hole 541 and the second through hole 542 on the pick 54 rotate until to be aligned with the bottom end of the first foaming liquid tube 521 and the bottom end of the second foaming liquid tube 522, liquid in the first foaming liquid tube 521 and the second foaming liquid tube 522 flows into the mixing tube 53, the electric motor drives the agitating vane 56 to rotate through the rotary shaft, the agitating vane 56 can stir the polyether and isocyanate, so that the two solutions are mixed more uniformly, thereby improving the reaction rate and obtaining the polyurethane foam. The polyurethane foam obtained through the reaction will enter into the expansion bin 17 and be adhered to the net structure 171, the polyurethane foam will fill the gap in the net structure 171 quickly, so as to complement the volume of the auxiliary equipment; and finally, the buoyancy of the auxiliary equipment is recovered to be normal.

Figure 2:
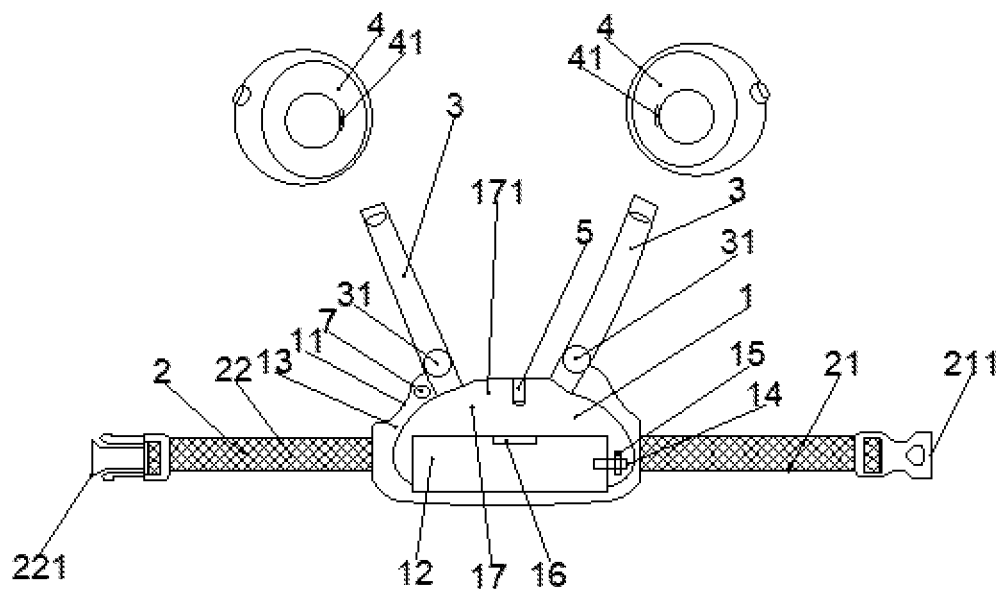
FIG. 2 is a schematic diagram of an unfolding state of piece of swimming auxiliary equipment provided by embodiments of the present disclosure.
Figure 3:
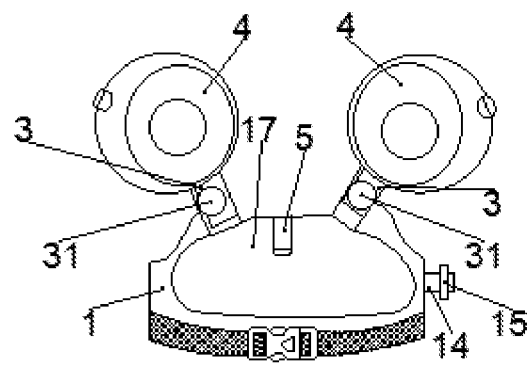
FIG. 3 is a front view of a wearing state of a swimming auxiliary equipment provided by embodiments of the present disclosure.
Figure 4:
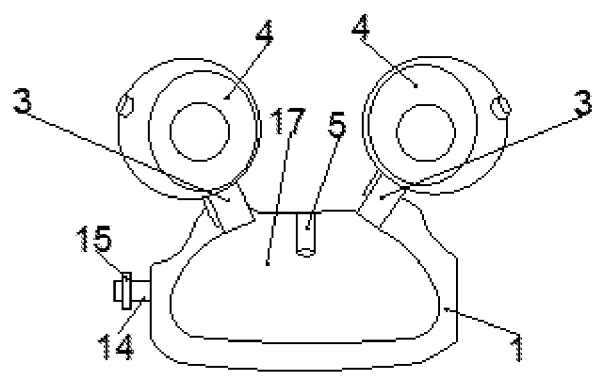
FIG. 4 is a rear view of a wearing state of a swimming auxiliary equipment provided by embodiments of the present disclosure.
Figure 5:
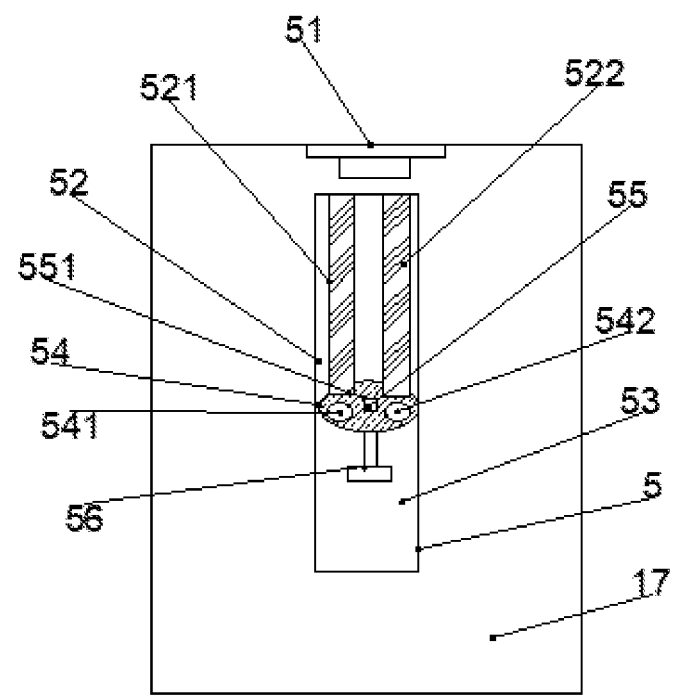
FIG. 5 is a structural schematic diagram of a priming device in a swimming auxiliary equipment provided by embodiments of the present disclosure.

As shown in FIG. 1 to FIG. 2, in one embodiment, the strap 2 includes a first waistband 21 and a second waistband 22, one end of the first waistband 21 is connected to the auxiliary equipment main body 1, and the other end of the first waistband 21 is provided with a slot 211; and one end of the second waistband 22 is connected to the auxiliary equipment main body 1, the other end of the second waistband 22 is provided with a buckle 221, and the buckle 221 is clamped in the slot 211.

In this embodiment, the auxiliary equipment main body 1 fits with the waist of the human body, the clamping position of the first waistband 21 and the second waistband 22 can be subjected to suitability adjustment according to the body form; and when it is adjusted to the suitable position, the buckle 221 is clamped in the slot 211, so that the first waistband 21 is locked with the second waistband 22. The first waistband 21 and the second waistband 22 can be made of rubber, the length of the first waistband 21 and the second waistband 22 can be subjected to contraction adjustment, so as to be convenient for users.

Based on the above implementation mode, the present disclosure further includes the following embodiments.

Figure 6:
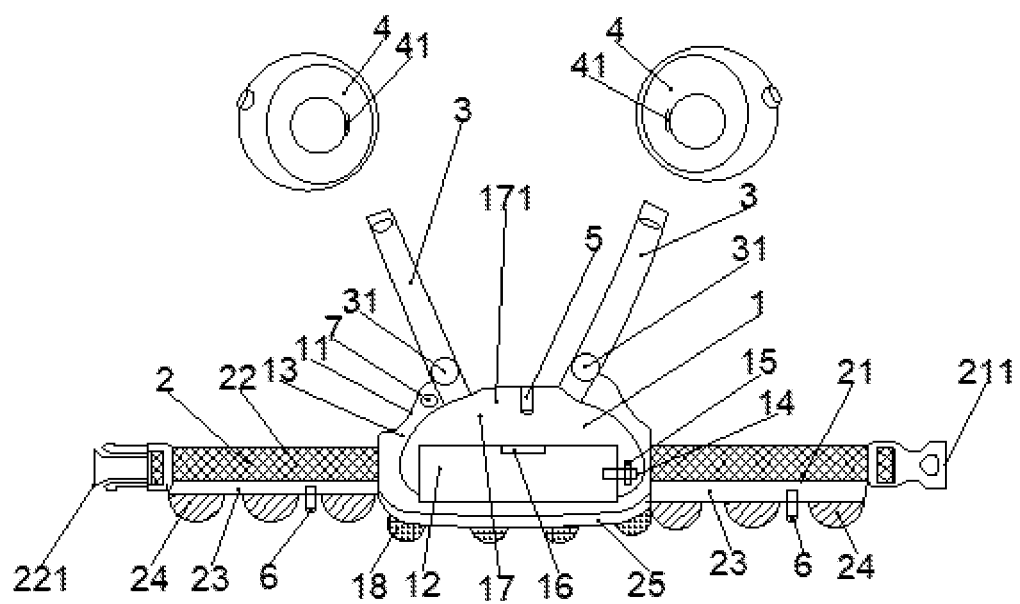
FIG. 6 is a schematic diagram of another structure of a swimming auxiliary equipment provided by embodiments of the present disclosure.
Figure 7:
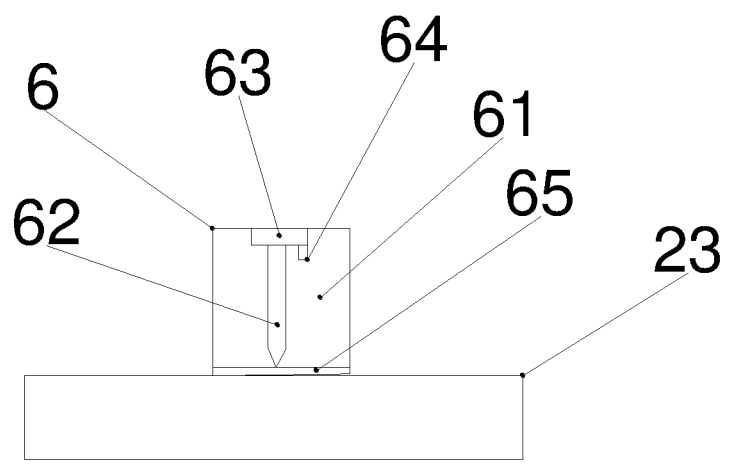
FIG. 7 is a structural schematic diagram of a gas injection device in a swimming auxiliary equipment provided by embodiments of the present disclosure.

As shown in FIG. 6 to FIG. 7, in one embodiment, outer walls of the first waistband 21 and the second waistband 22 are all connected to a second air bag 23, an outer wall of the auxiliary equipment main body 1 is connected to a third air bag 25, and an outer wall of the second air bag 23 and an outer wall of the third air bag 25 are all provided with gas injection devices 6; and each gas injection device 6 includes a gas storage tank 61, a rotary rod 62 and a motor 63, diaphragms 65 are arranged between the gas storage tank 61 and the second air bag 23 as well as between the gas storage tank 61 and the third air bag 25, the motor 63 is arranged on an inner wall of the gas storage tank 61, an input end of the motor 63 is connected to a second controller 64, the second controller 64 is in communication connection with the pressure sensor 16, an output end of the motor 63 is connected to the rotary rod 62, and the rotary rod 62 resists to the diaphragms 65.

A plurality of first air flotation bins 24 are uniformly arranged on the second air bag 23, a plurality of second air flotation bins 18 are uniformly arranged on the outer wall of the third air bag 25, the first air flotation bins 24 are communicated with the second air bag 23, and the second air flotation bins 18 are communicated with the third air bag 25; and the first air flotation bins 24 and the second air flotation bins 18 are located on the same plane, and the volume of the second air flotation bins 18 is greater than that of the first air flotation bins 24.

In this embodiment, the gas injection devices 6 are respectively arranged on the second air bag 23 and the third air bag 25, and high pressure carbon dioxide is stored in the gas storage tank 61 of each gas injection device 6. When the pressure in the auxiliary equipment main body 1 drops sharply, the pressure sensor 16 will transmit the detected pressure signal to the second controller 64 in the gas injection device 6 in a wireless form, the second controller 64 controls the motor to start, the motor 63 drives the rotary rod 62 in the gas storage tank 61 to rotate, the bottom end of the rotary rod 62 may drill the diaphragm 65 between the gas storage tank 61 and the second air bag 23 and the diaphragm 65 between the gas storage tank 61 and the third air bag 25, so that the gas injection device 6 is respectively communicated with the second air bag 23 and the third air bag 25, and the high pressure carbon dioxide in the gas storage tank 61 will flow into the second air bag 23 and the third air bag 25 quickly, so that the volume of the whole auxiliary equipment increases quickly. In addition, the plurality of first air flotation bins 24 are arranged on the outer walls of the first waistband 21 and the second waistband 22 with equal spacing, the plurality of second air flotation bins 18 are arranged on the third air bag 25 with equal spacing, the volume of the second air flotation bins 18 is designed to be greater than that of the first air flotation bins 24, so that the volume around the auxiliary equipment is uniformly distributed, the buoyancy of the whole auxiliary equipment can keep balance to avoid rollover, thereby further improving the use and safety performances of the auxiliary equipment.

As shown in FIG. 6, in one embodiment, inner walls of the arm jackets 4 are provided with heart rate sensors 41, which are in communication connection with the second controller 64.

In this embodiment, in order to avoid buoyancy compensation for the auxiliary equipment caused by misjudgment, the heart rate sensors 41 are installed at the arm jackets 4, and the heart rate sensors 41 can detect the heart rate change of human body. When air leakage occurs to the auxiliary equipment, the user will be restless. At this time, the heart rate of the human body will increase, the second controller 64 will comprehensively judge the pressure in the auxiliary equipment and the heart rate change of the human body so as to control the starting of the gas injection device 6, thereby ensuring the using reliability of the auxiliary equipment.

As shown in FIG. 6, in one embodiment, the connecting belt 3 is an annular belt, on which a lock catch is arranged.

In this embodiment, two arm jackets 4 are provided and tied to the elbow of the human body through the strap 3, the length of the connecting belt 3 can be adjusted, after being adjusted to the suitable length, the connecting belt 3 is locked through the lock catch 31, so it is suitable for different users.

In another embodiment, a safety module is arranged in the auxiliary equipment main body 1, a waterproof layer is arranged outside the safety module, and the safety module includes a voice prompt module, a vital sign monitoring module and a help module; and an output end of each heart rate sensor is connected to an input end of the vital sign monitoring module, an output end of the vital sign monitoring module is in communication connection with an input end of the help module, and an output end of the help module is in communication connection with the voice prompt module.

Specifically, when the user wears the auxiliary equipment, the voice prompt module will send out voice prompt of "please wear the auxiliary equipment correctly, confirm the correct lock, and finish the warm-up", and the voice prompt is repeated for three times; correctly wearing the auxiliary equipment is an effective method to prevent drowning, therefore it is very necessary to prompt the user to wear the auxiliary equipment correctly; and the warm-up before swimming can avoid convulsions, strain and other dangerous situations during swimming.

The vital sign monitoring module receives the data of the heart rate sensors 41 in the arm jackets 4 so as to judge whether the heart rate of the user is normal or abnormal, and usually the normal heart rate scope is 60-100 beats/minute. The user uses the swimming auxiliary equipment usually in the swimming state, with the change of the heart rate. In the normal swimming state, the heart rate will keep a higher state (such as, greater than 70 beats/minute) due to continuous movement, but the heart rate is relatively stable. In the event of drowning, the heart rate will increase at the beginning of drowning, the heart rate will weaken and be lower than the normal heart rate scope at the end of drowning, even the heart rate will disappear in a dangerous situation. The vital sign monitoring module can judge whether the user is normal according to the heart rate of the user, when the heart rate of the user is changed within the scope of 60-100 beats/minute, and the maximum value of the heart rate is greater than 70 beats/minute, the maximum value is stable, and it judges that the user is normal; when the heart rate of the user fluctuates within the scope of 60-100 beats/minute and keeps stable, it judges that the user is normal; when the heart rate of the user exceeds the scope of 60-100 beats/minute, is reduced at a high speed and reduced quickly, and then it is continuously reduced below 50 beats/minute, it judges that the user is abnormal;

A GPS locator is arranged in the help module, the help module receives the information of the vital sign monitoring module, and when the user is normal, the positioning sent by the GPS locator of the help module is displayed as a circle shape; and when the user is abnormal, the positioning sent by the GPS locator of the help module is displayed as a SOS shape, and the voice prompt module is controlled to send out a help voice signal. A rescuer adopts a rescue application program matching with the safety module in this embodiment, so as to clearly see the positioning information sent by the user; when there is SOS shape, the rescuer may rescue the user according to the positioning information immediately, so as to ensure that the user can be rescued in time when in danger; and the help voice signal sent by the voice prompt module can promote the nearby personnel to find the user for rescuing the user.

In addition, an external trigger button 7 is arranged, the external trigger button 7 is in signal connection with the safety module and arranged on the auxiliary equipment main body 1, and by manually triggering the external trigger button 7, the positioning sent by the GPS locator of the help module is displayed as the SOS shape, and the rescuer can rescue the user immediately according to the positioning information.

For the above description of the embodiment, those of professional skill in the art may realize or use the present disclosure. A plurality of modifications to these embodiments are apparent to those of professional skill in the art, and the general principles defined in the present disclosure may be achieved in other embodiments without deviating from the spirit and scope of the present disclosure. Therefore, the present disclosure is not limited to these embodiments shown in the present disclosure, and meets the widest range consistent to the principle and novel features of the present disclosure.

What is claimed is:

1. A swimming auxiliary equipment, comprising an auxiliary equipment main body, a strap, a connecting belt and two arm jackets, wherein two sides of the auxiliary equipment main body are tied to the waist of a swimmer through the strap, and the two arm jackets are all connected to the auxiliary equipment main body through the connecting belt; the auxiliary equipment main body comprises a waterproof layer and a first air bag, a cavity is arranged inside the waterproof layer, the first air bag is arranged in the cavity and connected to an outside air pump through an inflatable head, a pneumatic one-way valve is arranged on the inflatable head, and a pressure sensor is arranged on an inner wall of the auxiliary equipment main body; and the auxiliary equipment main body further comprises an expansion bin, which is arranged in the cavity and comprises a net structure with a plurality of connected layers, the net structure is a flexible structure, a priming device is connected to the net structure and arranged in the cavity, and the priming device is in signal connection with the pressure sensor.

2. The swimming auxiliary equipment according to claim 1, wherein the priming device comprises a sealing cover, a liquid storage tube and a mixing tube, a top end of the liquid storage tube is connected to the sealing cover, a bottom end of the liquid storage tube is connected to a top end of the mixing tube, a bottom end of the mixing tube is connected to the net structure, and a pick is also connected between the liquid storage tube and the mixing tube; and a first foaming liquid tube and a second foaming liquid tube that are independent of each other are arranged in the liquid storage tube, a top end of the first foaming liquid tube and a top end of the second foaming liquid tube are all in sealing connection with the sealing cover, a bottom end of the first foaming liquid tube and a bottom end of the second foaming liquid tube all resist to the pick, a first through hole and a second through hole that adapt to the bottom end of the first foaming liquid tube and the bottom end of the second foaming liquid tube are formed in the pick, an upper surface of the pick is connected to a rotary motor, a first controller is arranged in the rotary motor, and the first controller is in communication connection with the pressure sensor.

3. The swimming auxiliary equipment according to claim 2, wherein an electric motor is arranged at the lower part of the pick, and the electric motor is connected to an agitating vane through a rotary shaft; and when the first through hole and the second through hole on the pick rotate until to be aligned with the bottom end of the first foaming liquid tube and the bottom end of the second foaming liquid tube, liquid in the first foaming liquid tube and the second foaming liquid tube flows into the mixing tube, and the electric motor drives the agitating vane to rotate.

4. The swimming auxiliary equipment according to claim 1, wherein the strap comprises a first waistband and a second waistband, one end of the first waistband is connected to the auxiliary equipment main body, and the other end of the first waistband is provided with a slot; and one end of the second waistband is connected to the auxiliary equipment main body, the other end of the second waistband is provided with a buckle, and the buckle is clamped in the slot.

5. The swimming auxiliary equipment according to claim 4, wherein outer walls of the first waistband and the second waistband are all connected to a second air bag an outer wall of the auxiliary equipment main body is connected to a third air bag, and an outer wall of the second air bag and an outer wall of the third air bag are all provided with gas injection devices.

6. The swimming auxiliary equipment according to claim 5, wherein each gas injection device comprises a gas storage tank, a rotary rod and a motor, diaphragms are arranged between the gas storage tank and the second air bag as well as between the gas storage tank and the third air bag, the motor is arranged on an inner wall of the gas storage tank, an input end of the motor is connected to a second controller, the second controller is in communication connection with the pressure sensor, an output end of the motor is connected to the rotary rod, and the rotary rod resists to the diaphragms.

7. The swimming auxiliary equipment according to claim 6, wherein a plurality of first air flotation bins are uniformly arranged on the second air bag, a plurality of second air flotation bins are uniformly arranged on the outer wall of the third air bag, the first air flotation bins are communicated with the second air bag, and the second air flotation bins are communicated with the third air bag; and the first air flotation bins and the second air flotation bins are located on the same plane, and the volume of the second air flotation bins is greater than that of the first air flotation bins.

8. The swimming auxiliary equipment according to claim 7, wherein inner walls of the arm jackets are provided with heart rate sensors, which are in communication connection with the second controller.

9. The swimming auxiliary equipment according to claim 1, wherein the connecting belt is an annular belt, on which a lock catch is arranged.

10. The swimming auxiliary equipment according to claim 8, wherein a safety module is arranged in the auxiliary equipment main body, and the safety module comprises a voice prompt module, a vital sign monitoring module and a help module; and an output end of each heart rate sensor is connected to an input end of the vital sign monitoring module, an output end of the vital sign monitoring module is in communication connection with an input end of the help module, and an output end of the help module is in communication connection with the voice prompt module.

* * * * *